(12) United States Patent
Hsieh et al.

(10) Patent No.: US 8,501,811 B2
(45) Date of Patent: Aug. 6, 2013

(54) TASPASE1 INHIBITORS AND THEIR USES

(75) Inventors: James Hsieh, St. Louis, MO (US);
Emily Cheng, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 13/162,992

(22) Filed: Jun. 17, 2011

(65) Prior Publication Data

US 2012/0015990 A1 Jan. 19, 2012

Related U.S. Application Data

(60) Provisional application No. 61/355,612, filed on Jun. 17, 2010.

(51) Int. Cl.
*A61K 31/175* (2006.01)
*A61K 31/519* (2006.01)
*A61K 31/41* (2006.01)
*A61K 31/415* (2006.01)

(52) U.S. Cl.
USPC ......... 514/581; 514/261.1; 514/381; 514/406

(58) Field of Classification Search
None
See application file for complete search history.

(56) References Cited

U.S. PATENT DOCUMENTS 5,863,936 A * 1/1999 Gaeta et al. .................... 514/443
6,794,400 B2 * 9/2004 Cai et al. ........................ 514/357

OTHER PUBLICATIONS

[Book] Goodman & Goldman's The Pharmacological Basis of Therapeutics, Ninth Edition (1996), Appendix II, pp. 1707-1711.
[Book] Goodman & Goldman's The Pharmacological Basis of Therapeutics, Tenth Edition (2001), Appendix II, pp. 475-493.
[Book] Physicians Desk Reference (e.g., 2005, 59th edition or the online version).

Takeda, Proteolysis of MLL family proteins is essential for taspase1-orchestrated cell cycle progression, Genes Dev, 2006, pp. 2397-2409, vol. 20.
Niehof, EPS15R, TASP1, and PRPF3 are novel disease candidate genes targeted by HNF4alpha splice variants in hepatocellular carcinomas, Gastroenterology, 2008, pp. 1191-1202, vol. 134.
Scrideli, 2008, Gene expression profile analysis of primary glioblastomas and non-neoplastic brain tissue: identification of potential target genes by oligonucleotide microarray and real-time quantitative PCR, J Neurooncol, 2008, pp. 281-291, vol. 88.
Hsieh, Taspase1: a threonine aspartase required for cleavage of MLL and proper HOX gene expression, Cell, 2003, pp. 293-303, vol. 115.
Lee, Design, syntheses, and evaluation of Taspase1 inhibitors, Bioorg Med Chem Lett, 2009, pp. 5086-5090, vol. 19.
Zha, Posttranslational N-myristoylation of BID as a molecular switch for targeting mitochondria and apoptosis, Science, 2000, pp. 1761-1765, vol. 290.
Thornberry, A combinatorial approach defines specificities of members of the caspase family and granzyme B. Functional relationships established for key mediators of apoptosis, J Biol Chem, 1997, pp. 17907-17911, vol. 272.
Khan, Crystal structure of human Taspase1, a crucial protease regulating the function of MLL, Structure, 2005, pp. 1443-1452, vol. 13.
Shoemaker, The NCI60 human tumour cell line anticancer drug screen, Nat Rev Cancer, 2006, pp. 813-823, vol. 6.
Saunders, Identification of small-molecule inhibitors of autotaxin that inhibit melanoma cell migration and invasion, Mol Cancer Ther, 2008, pp. 3352-3362, vol. 7.
Chen, Taspase1 Functions as a Non-Oncogene Addiction Protease that Coordinates Cancer Cell Proliferation and Apoptosis, Cancer Res, Jul. 1, 2010, pp. 5358-5367, vol. 70, No. 13.
Chen, A Pharmacologic Inhibitor of the Protease Taspase1 Effectively Inhibits Breast and Brain Tumor Growth, Cancer Res, Feb. 1, 2012, pp. 736-746, vol. 72, No. 3.
Knauer, Bioassays to Monitor Taspase1 Function for the Identification of Pharmacogenetic Inhibitors, PLoS One, May 2011, pp. 1-14, vol. 6, Issue 5.

* cited by examiner

*Primary Examiner* — James D Anderson
(74) *Attorney, Agent, or Firm* — Polsinelli PC

(57) ABSTRACT

Provided herein are small molecule inhibitors of Taspase1 and methods of using the small molecule inhibitors of Taspase1 to treat neoplasm in subjects in need thereof.

1 Claim, 12 Drawing Sheets
(7 of 12 Drawing Sheet(s) Filed in Color)

C Ac-ISQLD-vinyl sulfone

D

SEQUENCE LISTING

<160> NUMBER OF SEQ ID NOS: 15

<210> SEQ ID NO 1
<211> LENGTH: 20
<212> TYPE: PRT
<213> ORGANISM: Artificial Sequence
<220> FEATURE:
<223> OTHER INFORMATION: COMPLETELY SYNTHESIZED
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 1

Xaa Xaa Xaa Pro Xaa Ile Xaa Gln Leu Asp Gly Xaa Asp Asp Xaa Ser
1               5                   10                  15

Xaa Ser Asp Xaa
            20

<210> SEQ ID NO 2
<211> LENGTH: 20
<212> TYPE: PRT
<213> ORGANISM: Homo sapiens

<400> SEQUENCE: 2

Gly Lys Arg Ser Ala Glu Gly Gln Val Asp Gly Ala Asp Asp Leu Ser
1               5                   10                  15

Thr Ser Asp Glu
            20

<210> SEQ ID NO 3
<211> LENGTH: 20
<212> TYPE: PRT
<213> ORGANISM: Homo sapiens

<400> SEQUENCE: 3

Cys Asp Leu Pro Lys Ile Ser Gln Leu Asp Gly Val Asp Asp Gly Thr
1               5                   10                  15

Glu Ser Asp Thr
            20

<210> SEQ ID NO 4
<211> LENGTH: 20
<212> TYPE: PRT
<213> ORGANISM: Mus musculus

<400> SEQUENCE: 4

Gly Lys Arg Ser Ala Glu Gly Gln Val Asp Gly Ala Asp Asp Leu Ser
1               5                   10                  15

Thr Ser Asp Glu
            20

<210> SEQ ID NO 5
<211> LENGTH: 20
<212> TYPE: PRT
<213> ORGANISM: Mus musculus

<400> SEQUENCE: 5

Cys Asp Leu Pro Lys Ile Ser Gln Leu Asp Gly Val Asp Asp Gly Thr
1               5                   10                  15

Glu Ser Asp Thr
            20

<210> SEQ ID NO 6
<211> LENGTH: 20
<212> TYPE: PRT
<213> ORGANISM: Danio rerio

<400> SEQUENCE: 6

Ser Lys Arg Ser Ala Glu Gly Gln Val Asp Gly Ala Asp Asp Met Ser
1               5                   10                  15

Thr Ser Ser Ser
            20

<210> SEQ ID NO 7
<211> LENGTH: 20
<212> TYPE: PRT
<213> ORGANISM: Danio rerio

<400> SEQUENCE: 7

Leu Glu Leu Gln Gln Ile Gly Gln Leu Asp Gly Val Asp Asp Gly Ser
1               5                   10                  15

Glu Ser Asp Ile
            20

<210> SEQ ID NO 8
<211> LENGTH: 20
<212> TYPE: PRT
<213> ORGANISM: Homo sapiens

<400> SEQUENCE: 8

Pro Gly Ala Pro Arg Ile Glu Gln Leu Asp Gly Val Asp Asp Gly Thr
1               5                   10                  15

Asp Ser Glu Ala
            20

<210> SEQ ID NO 9
<211> LENGTH: 20
<212> TYPE: PRT
<213> ORGANISM: Mus musculus

```
<400> SEQUENCE: 9

Ala Gly Ala Pro Arg Ile Glu Gln Leu Asp Gly Val Asp Asp Gly Thr
1               5                   10                  15

Asp Ser Glu Ala
            20

<210> SEQ ID NO 10
<211> LENGTH: 20
<212> TYPE: PRT
<213> ORGANISM: Drosophila melanogaster

<400> SEQUENCE: 10

Ala Ala Lys Met Arg Ile Met Gln Met Asp Gly Val Asp Asp Ser Ile
1               5                   10                  15

Thr Glu Phe Arg
            20

<210> SEQ ID NO 11
<211> LENGTH: 20
<212> TYPE: PRT
<213> ORGANISM: Homo sapiens

<400> SEQUENCE: 11

Thr Gln Ala Pro Leu Val Leu Gln Val Asp Gly Thr Gly Asp Thr Ser
1               5                   10                  15

Ser Glu Glu Asp
            20

<210> SEQ ID NO 12
<211> LENGTH: 20
<212> TYPE: PRT
<213> ORGANISM: Mus musculus

<400> SEQUENCE: 12

Gln Gln Ala Pro Leu Val Leu Gln Val Asp Gly Thr Gly Asp Thr Ser
1               5                   10                  15

Ser Glu Glu Asp
            20

<210> SEQ ID NO 13
<211> LENGTH: 20
<212> TYPE: PRT
<213> ORGANISM: Danio rerio

<400> SEQUENCE: 13

Gln Gln Pro Pro Met Met Leu Gln Val Asp Gly Ala Gly Asp Thr Ser
1               5                   10                  15

Ser Glu Glu Asp
            20

<210> SEQ ID NO 14
<211> LENGTH: 20
<212> TYPE: PRT
<213> ORGANISM: Drosophila melanogaster

<400> SEQUENCE: 14

Lys Thr Leu Ala Ala Ala Lys Gln Leu Asp Gly Ala Leu Asp Ser Ser
1               5                   10                  15

Asp Glu Asp Glu
            20
```

```
<210> SEQ ID NO 15
<211> LENGTH: 20
<212> TYPE: PRT
<213> ORGANISM: Drosophila melanogaster

<400> SEQUENCE: 15

Pro Met Asp Asp Ile Ile Glu Gln Leu Asp Gly Ala Gly Asp Leu Leu
1               5                   10                  15

Lys Leu Ser Glu
            20
```

TASPASE1 INHIBITORS AND THEIR USES

CROSS REFERENCE TO RELATED APPLICATIONS

This application claims the priority of U.S. provisional application No. 61/355,612, filed Jun. 17, 2010, which is hereby incorporated by reference in its entirety.

GOVERNMENTAL RIGHTS

This invention was made with government support under Rapid Access NCI Discovery (RAND) Resources Program, cycle 12, awarded by the National Cancer Institute. The United States Government has certain rights in this invention.

FIELD OF THE INVENTION

Provided herein are inhibitors of Taspase1 and methods of using the inhibitors of Taspase1 to treat a neoplasm in a subject.

BACKGROUND OF THE INVENTION

Marked advances in basic biomedical research have transformed the landscape of cancer treatment. However, despite these significant strides towards combating cancer, victory remains out of reach as most advance-staged cancer patients still succumb to their diseases. The majority of the current cancer treatment methods result in severe general toxicity to the human body. Both radiation and chemotherapy have deleterious effects to the host, causing significant morbidity and mortality. Thus, there is an urgent need for novel cancer therapeutics. More specifically, there is a need for novel targets and therapeutics aimed at these targets for more efficient yet less toxic strategies for cancer treatment.

SUMMARY OF THE INVENTION

One aspect of the present invention encompasses a compound comprising Formula (I):

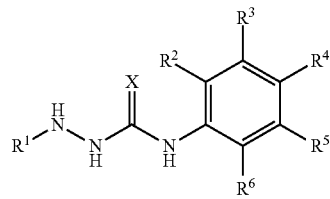

(I)

wherein:
$R^1$ is hydrocarbyl or substituted hydrocarbyl;
$R^2$, $R^3$, $R^4$, $R^5$, and $R^6$ are independently chosen from the group consisting of hydrogen, halogen, hydroxyl, amino, hydrocarbyl, and substituted hydrocarbyl; and
X is oxygen or sulfur.

Another aspect of the present invention encompasses a compound comprising Formula II:

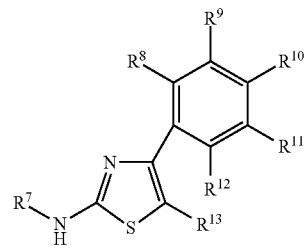

(II)

wherein:
$R^7$ is hydrocarbyl or substituted hydrocarbyl; and
$R^8$, $R^9$, $R^{10}$, $R^{11}$, and $R^{12}$ are independently chosen from the group consisting of hydrogen, halogen, hydroxyl, amino, hydrocarbyl, and substituted hydrocarbyl; and
$R^{13}$ is chosen from the group consisting of hydrogen, hydrocarbyl, and substituted hydrocarbyl.

Still another aspect of the present invention encompasses a method for treating a neoplasm in a subject in need thereof. The method comprises administering to the subject a therapeutic amount of a compound comprising Formula (I):

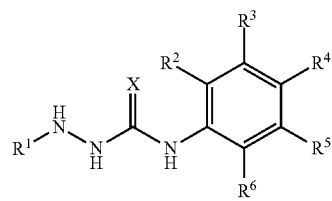

(I)

wherein:
$R^1$ is hydrocarbyl or substituted hydrocarbyl;
$R^2$, $R^3$, $R^4$, $R^5$, and $R^6$ are independently chosen from hydrogen, halogen, hydroxyl, amino, hydrocarbyl, and substituted hydrocarbyl; and
X is oxygen or sulfur.

Yet another aspect of the present invention encompasses a method for treating a neoplasm in a subject in need thereof, the method comprising administering to the subject a therapeutic amount of a compound comprising Formula (II):

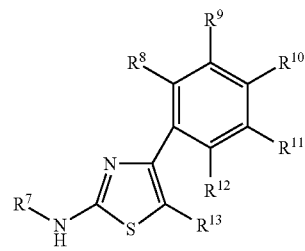

(II)

wherein:
$R^7$ is hydrocarbyl or substituted hydrocarbyl; and
$R^8$, $R^9$, $R^{10}$, $R^{11}$, and $R^{12}$ are independently chosen from hydrogen, halogen, hydroxyl, amino, hydrocarbyl, and substituted hydrocarbyl; and
$R^{13}$ is chosen from hydrogen, hydrocarbyl, or substituted hydrocarbyl.

Other aspects and iterations of the present application are detailed more thoroughly below.

REFERENCE TO COLOR FIGURES

The application file contains at least one photograph executed in color. Copies of this patent application publication with color photographs will be provided by the Office upon request and payment of the necessary fee.

DETAILED DESCRIPTION

Figure 1:
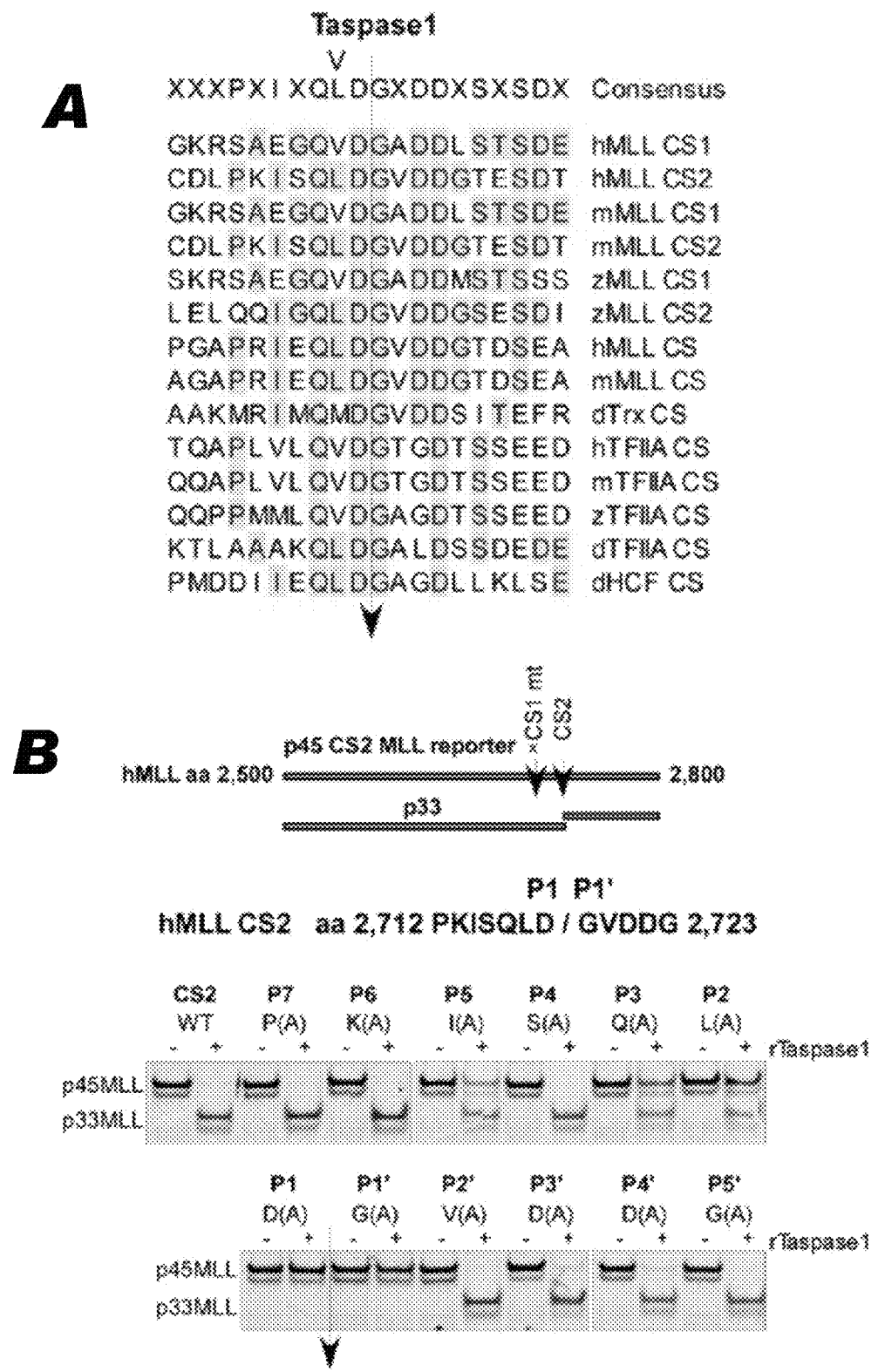
FIG. 1 illustrates the characterization of Taspase1 cleavage site. (A) Alignment of known Taspase1 cleavage sites (CS) identifies consensus sequences. h, m, z, and d denote human, mouse, zebra fish, and Drosophila, respectively. The consensus sequence is SEQ ID NO: 1, hMLL CS1 is SEQ ID NO: 2, hMLL CS2 is SEQ ID NO: 3, mMLL CS1 is SEQ ID NO: 4, mMLL CS2 is SEQ ID NO: 5, zMLL CS1 is SEQ ID NO: 6, zMLL CS2 is SEQ ID NO: 7, hMLL CS is SEQ ID NO: 8, mMLL CS is SEQ ID NO: 9, dTrx CS is SEQ ID NO: 10, hTFIIA CS is SEQ ID NO: 11, mTFIIA CS is SEQ ID NO: 12, zTFIIA CS is SEQ ID NO: 13, dTFIIA CS is SEQ ID NO: 14, and dHCF CS is SEQ ID NO: 15. (B) Alanine scanning mutagenesis of the Taspase1 cleavage site 2 on human MLL identifies critical amino acids required for Taspase1-mediated proteolysis. An hMLL CS2 only cleavage reporter (p45 CS2 MLL) was generated by mutations of the CS1 within the hMLL aa 2,500 to 2,800 polypeptide. The p45 CS2 MLL mutant reporters with alanine substitution of individual amino acid from P7 to P5' of the CS2 were generated and tested for Taspase1-mediated cleavage. The indicated IVTT, $^{35}$S methionine labeled p45 CS2-based MLL reporters were incubated with 15 ng of recombinant Taspase1 (rTaspase1) for 30 minutes at 30° C. The cleavage of p45 CS2 hMLL was resolved by SDS-PAGE and monitored by autoradiography.

Taspase1 (threonine aspartase 1, TASP-1) plays a role in the initiation and maintenance of cancers, and inhibition of Taspase1 may be an effective treatment for neoplasms or cancers. Provided herein are small molecule inhibitors of Taspase1. Also provided are methods for using the compounds of the invention to treat a neoplasm in a subject in need thereof.

(I) Compounds of the Invention

One aspect of the invention provides compounds comprising either Formula (I) or Formula (II). The compounds of the invention inhibit Taspase1 activity.

(a) Compounds Comprising Formula (I)

One aspect of the present invention provides a compound comprising Formula (I):

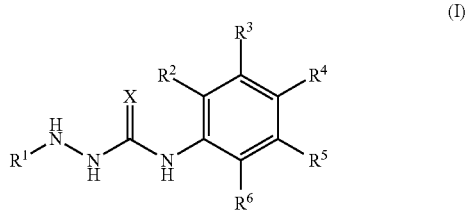

wherein:
$R^1$ is hydrocarbyl or substituted hydrocarbyl;
$R^2$, $R^3$, $R^4$, $R^5$, and $R^6$ are independently chosen from hydrogen, halogen, hydroxyl, amino, hydrocarbyl, and substituted hydrocarbyl; and
X is oxygen or sulfur.

In one embodiment, X may be sulfur. In another embodiment, $R^1$ may be carbocyclic, heterocyclic, substituted carbocyclic, or substituted heterocyclic. In a further embodiment, each of $R^2$, $R^3$, $R^4$, $R^5$, and $R^6$ may be hydrogen. In yet another embodiment, at least one of $R^2$, $R^3$, $R^4$, $R^5$, and $R^6$ may be halogen or haloalkyl. In an alternate embodiment, the compound comprising Formula (I) may have a structure as depicted in Table A.

In a preferred embodiment for compounds comprising Formula (I), $R^2$, $R^4$, $R^5$, and $R^6$ are each hydrogen, and $R^3$ is a haloalkyl. In a preferred alternative embodiment for compounds comprising Formula (I), $R^2$, $R^4$, $R^5$, and $R^6$ are each hydrogen, $R^3$ is haloalkyl, and $R^1$ is a substituted heterocyclic. In another preferred alternative of the embodiment, $R^1$ further comprises a carbonyl linkage. In an exemplary embodiment, the compound comprising Formula (I) comprises the structure of compound (1) as depicted in Table A.

In still another preferred embodiment for compounds comprising Formula (I), $R^2$, $R^3$, $R^4$, $R^5$, and $R^6$ are each hydrogen. In a preferred alternative of the embodiment for compounds comprising Formula (I), $R^2$, $R^3$, $R^4$, $R^5$, and $R^6$ are each hydrogen, and $R^1$ is a substituted heterocyclic. In another preferred alternative of the embodiment, $R^1$ further comprises a carbonyl linkage. In an exemplary embodiment, the compound comprising Formula (I) comprises the structure of compound (2) as depicted in Table A.

In yet another preferred embodiment for compounds comprising Formula (I), $R^2$, $R^4$, and $R^5$ are each hydrogen, and $R^3$ and $R^6$ are halogen. In a preferred alternative of the embodiment for compounds comprising Formula (I), $R^2$, $R^4$, and $R^5$ are each hydrogen, and $R^3$ and $R^6$ are halogen, and $R^1$ is a substituted carbocyclic. In another preferred alternative of the embodiment, $R^1$ comprises a {-}C(O)—CH$_2$—O—N=CH linkage. In an exemplary embodiment, the compound comprising Formula (I) comprises the structure of compound (3) as depicted in Table A.

In another preferred embodiment for compounds comprising Formula (I), $R^2$, $R^3$, and $R^5$ are each hydrogen, and $R^4$ and $R^6$ are halogen. In a preferred alternative embodiment for compounds comprising Formula (I), $R^2$, $R^3$, and $R^5$ are each hydrogen, and $R^4$ and $R^6$ are halogen, and $R^1$ is a substituted heterocyclic. In an exemplary embodiment, the compound comprising Formula (I) comprises the structure of compound (4) as depicted in Table A.

In yet another preferred embodiment for compounds comprising Formula (I), $R^2$, $R^5$, and $R^6$ are each hydrogen, and $R^3$ and $R^4$ are halogen. In a preferred alternative embodiment for compounds comprising Formula (I), $R^2$, $R^5$, and $R^6$ are each hydrogen, and $R^3$ and $R^4$ are halogen, and $R^1$ is substituted heterocyclic. In another preferred alternative of the embodiment, $R^1$ comprises a {-}C(O)—CH$_2$ linkage. In an exemplary alternative of the embodiment, the compound comprising Formula (I) comprises the structure of compound (5) as depicted in Table A.

In yet another preferred embodiment for compounds comprising Formula (I), $R^2$, $R^5$, and $R^6$ are each hydrogen, and $R^3$ and $R^4$ are halogen. In a preferred alternative embodiment for compounds comprising Formula (I), $R^2$, $R^5$, and $R^6$ are each hydrogen, and $R^3$ and $R^4$ are halogen, and $R^1$ is a carbocyclic. In another preferred alternative of the embodiment, $R^1$ further comprises a {—}C(S)—NH linkage. In an exemplary alternative of the embodiment, the compound comprising Formula (I) comprises the structure of compound (6) as depicted in Table A

TABLE A

| Compounds Comprising Formula (I) |
|---|
| 1 ![compound 1] |
| 2 ![compound 2] |

TABLE A-continued

Compounds Comprising Formula (I)

3

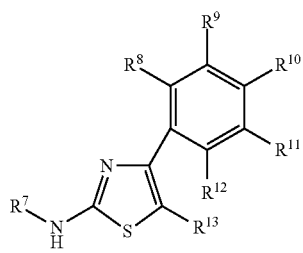

4

5

6

(b) Compounds Comprising Formula (II)

Another aspect of the invention encompasses a compound comprising Formula (II):

$$\text{(II)}$$

wherein:
$R^7$ is hydrocarbyl or substituted hydrocarbyl; and
$R^8$, $R^9$, $R^{10}$, $R^{11}$, and $R^{12}$ are independently chosen from hydrogen, halogen, hydroxyl, amino, hydrocarbyl, and substituted hydrocarbyl; and
$R^{13}$ is chosen from hydrogen, hydrocarbyl, or substituted hydrocarbyl.

In one embodiment, $R^7$ may be carbocyclic, heterocyclic, heteroaryl, substituted carbocyclic, substituted heterocyclic, or substituted heteroaryl. In an iteration of this embodiment, $R^7$ may further comprise a {—}(O)S(O){—} linkage. In another embodiment, $R^8$, $R^9$, $R^{10}$, $R^{11}$, and $R^{12}$ may be hydrogen, halogen, alkyl, or substituted alkyl. In a further embodiment, $R^8$, $R^9$, and $R^{12}$ may be hydrogen, $R^{10}$ may be alkyl, and $R^{11}$ may be halogen. In still another embodiment, $R^{13}$ may be hydrogen, alkyl, or substituted alkyl. In yet another embodiment, the compound comprising Formula (II) may have a structure as depicted in Table B.

In a preferred embodiment for compounds comprising Formula (II), $R^{13}$ may be alkyl, $R^8$, $R^9$, and $R^{12}$ are hydrogen, and $R^{10}$ and $R^{11}$ may be hydrogen, halogen, alkyl, or substituted alkyl. In a preferred alternative of the embodiment for compounds comprising Formula (II), $R^{13}$ is a methyl group, $R^8$, $R^9$, and $R^{12}$ are hydrogen, $R^{10}$ is a methyl group and $R^{11}$ is a halogen.

For each of the foregoing embodiments, $R^7$ may be carbocyclic, heterocyclic, heteroaryl, substituted carbocyclic, substituted heterocyclic, or substituted heteroaryl and may further comprise a {—}(O)S(O){—} linkage.

In a more preferred alternative of the embodiment for compounds comprising Formula (II), $R^{13}$ is a methyl group, $R^8$, $R^9$, and $R^{12}$ are hydrogen, $R^{10}$ is a methyl group, $R^{11}$ is a halogen $R^7$ is a substituted carbocyclic and further comprises a {—}(O)S(O){—} linkage. In an exemplary alternative of the embodiment, the compound comprising Formula (II) comprises the structure of compound (7) as depicted in Table B.

In another more preferred alternative of the embodiment for compounds comprising Formula (II), $R^{13}$ is a methyl group, $R^8$, $R^9$, and $R^{12}$ are hydrogen, $R^{10}$ is a methyl group, $R^{11}$ is a halogen $R^7$ is a substituted heterocyclic and further comprises a {—}(O)S(O){—} linkage. In an exemplary alternative of the embodiment, the compound comprising Formula (II) comprises the structure of compound (8) as depicted in Table B.

TABLE B

Compounds Comprising Formula (II)

7

8

(II) Compositions of the Invention

An additional aspect of the invention provides pharmaceutical compositions comprising either a compound comprising Formula (I) or Formula (II) and at least one pharmaceutically acceptable excipient. Compounds comprising Formula (I) are detailed above in section (I)(a) and compounds comprising Formula (II) are detailed above in section (I)(b).

The amount of the compound comprising Formulas (I) or (II) in the pharmaceutical composition may range from about 1%, about 3%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, or about 99% by weight of the total pharmaceutical composition.

(a) Excipients

A variety of excipients commonly used in pharmaceutical compositions may be selected on the basis of several criteria such as, e.g., the desired dosage form and the release profile properties of the dosage form. Non-limiting examples of suitable excipients include diluents, binders, fillers, buffering agents, pH modifying agents, effervescent disintegrants, non-effervescent disintegrants, dispersing agents, stabilizers, preservatives, compaction agents, lubricants, coloring agents, flavoring agents, sweeteners, taste masking agents, and combinations thereof. The amount and types of excipients utilized to form pharmaceutical compositions may be selected according to known principles of pharmaceutical science.

In one embodiment, the excipient may comprise at least one diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lacitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may comprise a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In yet another embodiment, the excipient may include a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Representative examples of suitable buffering agents include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be sodium carbonate, sodium bicarbonate, citric acid, malic acid, or tartaric acid.

In a further embodiment, the excipient may include a non-effervescent disintegrant. Suitable examples of non-effervescent disintegrants include, but are not limited to, starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth.

In another embodiment, the excipient may comprise an effervescent disintegrant. By way of non-limiting example, suitable effervescent disintegrants include sodium bicarbonate in combination with citric acid and sodium bicarbonate in combination with tartaric acid.

In another alternate embodiment, the excipient may also include a preservative. Non-limiting examples of suitable preservatives include antioxidants, such as alpha-tocopherol or ascorbate, and antimicrobials, such as parabens, chlorobutanol or phenol.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In a further embodiment, the excipient may include a lubricant. Non-limiting examples of suitable lubricants include minerals such as talc or silica; and fats such as vegetable stearin, magnesium stearate or stearic acid.

In still another embodiment, it may be desirable to provide a coloring agent. Suitable color additives include, but are not limited to, food, drug and cosmetic colors (FD&C), drug and cosmetic colors (D&C), or external drug and cosmetic colors (Ext. D&C).

In another embodiment, the excipient may comprise a flavoring agent. Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oil, such as lemon oil, orange oil, grape and grapefruit oil, fruit essences including apple, peach, pear, strawberry, raspberry, cherry, plum, pineapple, and apricot.

In yet another embodiment, the excipient may comprise a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In a further embodiment, the excipient may comprise a taste-masking agent. Taste-masking materials include cellulose hydroxypropyl ethers (HPC); low-substituted hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and combinations thereof.

The weight fraction of the excipient or combination of excipients in the tablet may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(III) Methods for Treating a Neoplasm

Another aspect encompasses use of a compound comprising Formula (I) or Formula (II) or a composition disclosed herein to treat a neoplasm in a subject in need thereof. The compounds comprising Formula (I) or Formula (II) are described above in section (I). Compositions comprising the compounds comprising Formula (I) or Formula (II) are detailed above in section (II).

(a) routes of Administration

The compound comprising Formula (I) or Formula (II) may be administered to the subject in accord with known methods, such as oral, systemic, or topical. Oral administration may be via solid dosage forms, such as tablets, capsules, pills, powders, granules, and the like. Alternatively, oral administration may be via liquid dosage forms, such as syrups, emulsions, solutions, suspensions, elixirs, and the like. Systemic administration includes intravenous, intramuscular, intraperitoneal, subcutaneous, intra-articular, intrasynovial, intrathecal, intrasternal, and the like. Typically, systemic administration comprises administration as a bolus, but it may also comprise continuous infusion over a period of time via a pump or the like. Preparations for systemic administration may be in the form of aqueous or non-aqueous isotonic sterile injection solutions or suspensions. Topical administration comprises transdermal or transmucosal (e.g., sublingual, nasal, inhalation, ocular, rectal, vaginal, and so forth). Preparations for topical administration may be in the form of solid dosage forms, aerosols, sprays, ointments, salves, gels, patches, creams, and the like. Those skilled in the art will appreciate that dosages and dosing schedules may be determined with guidance from Goodman & Goldman's The Pharmacological Basis of Therapeutics, Ninth Edition (1996), Appendix II, pp. 1707-1711, Goodman & Goldman's The Pharmacological Basis of Therapeutics, Tenth Edition (2001), Appendix II, pp. 475-493, and the Physicians Desk Reference (e.g., 2005, 59th edition or the online version).

(b) Treatment Regimes

In some embodiments, the compound comprising Formula (I) or Formula (II) may be administered alone. In other embodiments, the compound comprising Formula (I) or Formula (II) may be co-administered with another chemotherapeutic agent. The chemotherapeutic agent compound may be a cytotoxic agent that affects rapidly dividing cells in general, or it may be a targeted therapeutic agent that affects the deregulated proteins of malignant cells. The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, or combinations thereof.

Non-limiting examples of suitable alkylating agents include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lomustine (CCNU), mechlorethamine, mechlorethamine oxide hydrochloride, melphalan, meturedopa, nimustine, novembichin, phenesterine, piposulfan, prednimustine, ranimustine; temozolomide, thiotepa, triethylenemelamine, trietylenephosphoramide, triethylenethiophosphaoramide, trimethylolomelamine, trofosfamide, uracil mustard and uredopa. Suitable anti-metabolites include, but are not limited to aminopterin, ancitabine, azacitidine, 6-azauridine, capecitabine, carmofur (1-hexylcarbomoyl-5-fluorouracil), cladribine, cytarabine or cytosine arabinoside (Ara-C), dideoxyuridine, denopterin, doxifluridine, enocitabine, floxuridine, fludarabine, 5-fluorouracil, gemcetabine, hydroxyurea, leucovorin (folinic acid), 6-mercaptopurine, methotrexate, pemetrexed, pteropterin, thiamiprine, trimetrexate, and thioguanine. Non-limiting examples of suitable anti-tumor antibiotics include aclacinomysin, actinomycins, adriamycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, streptonigrin, streptozocin, tubercidin, valrubicin, ubenimex, zinostatin, and zorubicin. Non-limiting examples of suitable anti-cytoskeletal agents include colchicines, docetaxel, macromycin, paclitaxel, vinblastine, vincristine, vindesine, and vinorelbine. Suitable topoisomerase inhibitors include, but are not limited to, amsacrine, etoposide (VP-16), irinotecan, mitoxantrone, RFS 2000, teniposide, and topotecan. Non-limiting examples of suitable anti-hormonal agents such as aminoglutethimide, aromatase inhibiting 4(5)-imidazoles, bicalutamide, finasteride, flutamide, goserelin, 4-hydroxytamoxifen, keoxifene, leuprolide, LY117018, mitotane, nilutamide, onapristone, raloxifene, tamoxifen, toremifene, and trilostane. Examples of targeted therapeutic agents include, without limit, monoclonal antibodies such as alemtuzumab, epratuzumab, gemtuzumab, ibritumomab tiuxetan, rituximab, tositumomab, and trastuzumab; protein kinase inhibitors such as bevacizumab, cetuximab, dasatinib, erlotinib, gefitinib, imatinib, lapatinib, mubritinib, nilotinib, panitumumab, pazopanib, sorafenib, sunitinib, and vandetanib; angiogeneisis inhibitors such as angiostatin, endostatin, bevacizumab, genistein, interferon alpha, interleukin-2, interleukin-12, pazopanib, pegaptanib, ranibizumab, rapamycin, thalidomide; and growth inhibitory polypeptides such as erythropoietin, interleukins (e.g., IL-1, IL-2, IL-3, IL-6), leukemia inhibitory factor, interferons, thrombopoietin, TNF-α, CD30 ligand, 4-1BB ligand, and Apo-1 ligand. Also included are pharmaceutically acceptable salts, acids, or derivatives of any of the above listed agents.

The mode of administration of the chemotherapeutic agent can and will vary. Suitable modes of administration are detailed above in section (III)(a). The chemotherapeutic agent may be administered simultaneously, sequentially, or various combinations thereof. A skilled practitioner will be able to determine the appropriate dose of the chemotherapeutic agent.

(c) neoplasm

The neoplasm may be a benign neoplasm or it may be a malignant neoplasm (i.e., a cancer). The malignant neoplasm may be a primary cancer or it may be a secondary or metastatic cancer. The neoplasm may be early stage or late stage. Non-limiting examples of neoplasms that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood).

In certain embodiments, the neoplasm may be a malignant neoplasm such as brain cancer, breast cancer, colorectal cancer, leukemia, lung cancer, lymphoma, or prostate cancer.

(d) subjects

Suitable subjects include animals and humans. Non-limiting examples of suitable animals include companion animals such as cats, dogs, rodents, and horses; research animal such as mice, rats and other rodents; agricultural animals such as cows, cattle, pigs, goats, sheep, horses, deer, chickens and other fowl; zoo animals; and primates such as chimpanzees, monkeys, and gorillas. In one embodiment, the subject is a human.

DEFINITIONS

To facilitate understanding of the invention, several terms are defined below.

The term "acyl," as used herein alone or as part of another group, denotes the moiety formed by removal of the hydroxy group from the group COOH of an organic carboxylic acid, e.g., RC(O), wherein R is $R^1$, $R^1O-$, $R^1R^2N-$, or $R^1S-$, $R^1$ is hydrocarbyl, heterosubstituted hydrocarbyl, or heterocyclo, and $R^2$ is hydrogen, hydrocarbyl or substituted hydrocarbyl.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups having at least one carbon-carbon double bond that preferably contain from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups having at least one carbon-carbon triple bond that preferably contain from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkyl bridges, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroaryl" embraces unsaturated heterocyclyl radicals. Examples of unsaturated heterocyclyl radicals, also termed "heteroaryl" radicals include unsaturated 3 to 8 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 8-membered heteromonocyclic group containing an oxygen atom, for example, pyranyl, furyl, etc.; unsaturated 3 to 8-membered heteromonocyclic group containing a sulfur atom, for example, thienyl, etc.; unsaturated 3- to 8-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 8-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2, 5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. The term also embraces radicals where heterocyclyl radicals are fused with aryl radicals or a non-aromatic cyclic system. Examples of such fused bicyclic radicals include benzofuran, benzothiophene, and the like.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "neoplasm," as use herein, refers to the uncontrolled proliferation of abnormal cells. A solid neoplasm is a tumor. A neoplasm may be benign or malignant. Cells of a malignant neoplasm may invade surrounding tissues and may spread through the bloodstream and/or the lymphatic system to other parts of the body.

The terms "substituted hydrocarbyl," "substituted alkyl," "substituted alkenyl," "substituted aryl," "substituted heteroaryl," "substituted carbocylic," and "substituted homocyclic" as used herein refer to hydrocarbyl, alkyl, alkenyl, aryl, heteroaryl, carbocyclic, and heterocyclic moieties, respectively, that are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

As used herein, the terms "treating" or "treatment" refer to the act of treating a neoplasm, such that the rate of growth of the abnormal cells of the neoplasm is reduced or eliminated, the rate of cell division of the abnormal neoplastic cells is reduced or eliminated, the abnormal neoplastic cells are killed or die by apoptosis, the invasiveness of the abnormal neoplastic cells is reduced or eliminated, the metastasis of the abnormal neoplastic cells is reduced or eliminated, the progression of the neoplastic disorder is reduced or eliminated, the symptoms of the disorder are reduced or eliminated, the severity of the symptoms is reduced, and/or the reoccurrence of the symptoms is reduced or prevented.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds, compositions, and processes without departing from the scope of the invention, it is intended that all matter contained in the above description and in the examples given below, shall be interpreted as illustrative and not in a limiting sense.

EXAMPLES

The following examples illustrate several aspects of the invention.

Example 1

Characterization of Taspase1 Cleavage Motif

Genetic studies demonstrated that Taspase1 is required for cell proliferation and Taspase1$^{-/-}$ cells are resistant to oncogenic transformation. Furthermore, Taspase1 is over-expressed in human cancers, suggesting that Taspase1 may serve as a novel anticancer target [1,2,3]. To provide mechanistic insight into the substrate recognition by Taspase1, the Taspase1 cleavage consensus motif was characterized (FIG. 1A). Alanine scanning mutagenesis was performed on the cleavage site 2 (CS2, PKISQLD/GVDDG) of MLL1 to examine the importance of individual amino acids on Taspase1-mediated cleavage. Of note, MLL1 contains two Taspase1 cleavage sites (CS1 & CS2) that are positioned 53 amino acids (aa) apart, of which CS2 is known to be more efficiently processed (FIG. 1A) [4]. In vitro transcribed, translated (IVTT), $^{35}$S methionine labeled aa 2,500-2,800 of human MLL1, of which the CS1 is mutated, was employed as a CS2-specific cleavage reporter (p45 CS2 MLL). The cleavage of p45 CS2 MLL by recombinant Taspase1 (rTaspase1) was resolved by SDS-PAGE and examined by autoradiography. Data indicated that P1 aspartate and P1' glycine are essential, and P2 leucine, P3 glutamine, and P5 isoleucine are important for Taspase1-mediated proteolysis, whereas aspartates at P3' and P4' are dispensable (FIG. 1B). These data are consistent with the fact that P1 aspartate and P1' glycine are absolutely conserved, P2, P3, and P5 hydrophobic residues are conserved, and P4 is variable among the alignment of known Taspase1 cleavage motifs (FIG. 1A). Surprisingly, conserved P3' and P4' aspartates are dispensable, which likely reflect their regulatory instead of direct role in the substrate recognition by Taspase1.

Example 2

Design and Evaluation of Peptide-Based Taspase1 Inhibitors

Figure 2:
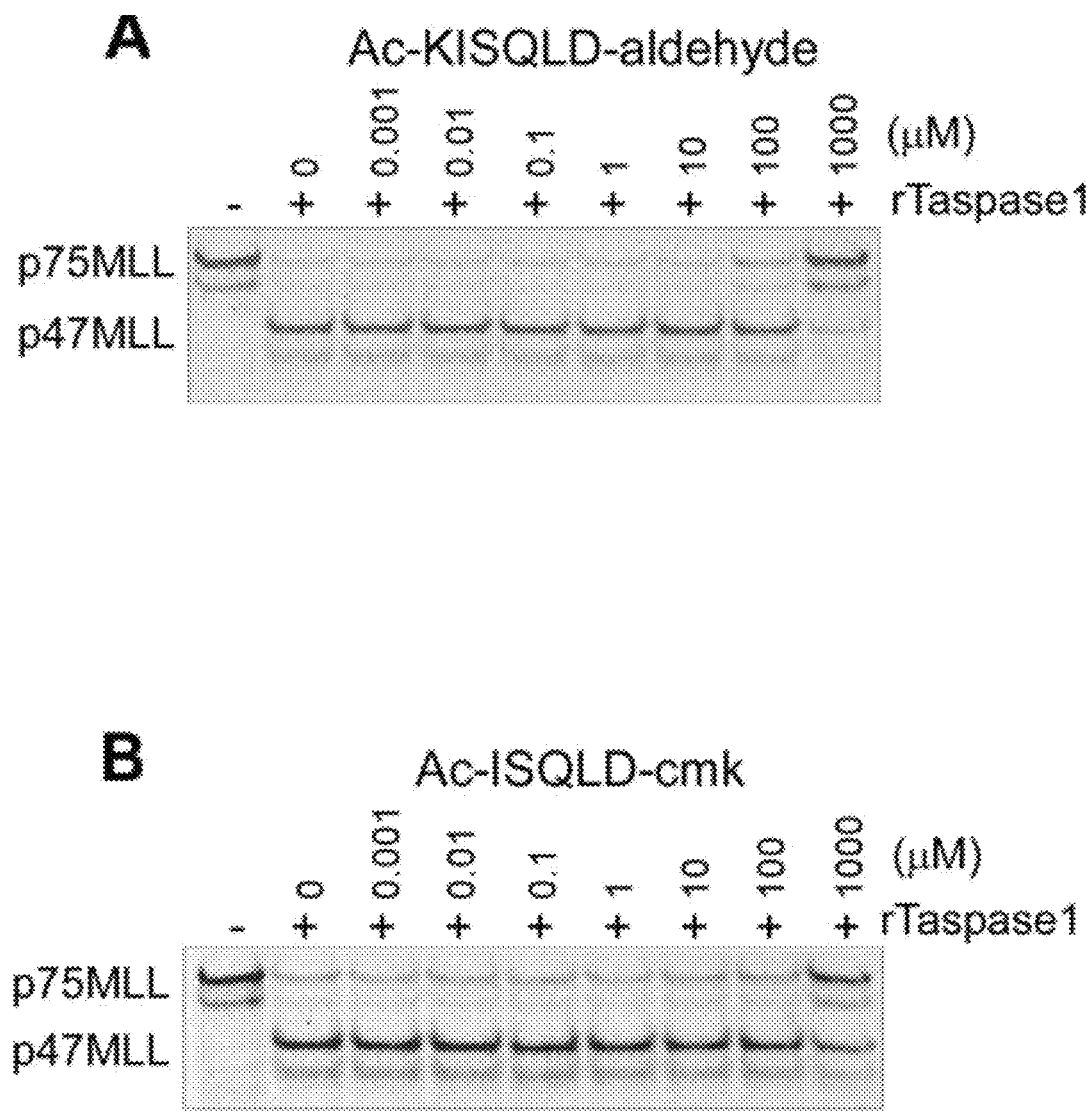
FIG. 2 depicts Taspase1 inhibition by ISQLD peptidomimetics and bortezomib. (A, B) Known functional groups against serine and cysteine proteases are not effective against Taspase1. Ac-KISQLD-aldehyde and Ac-ISQLD-cmk have minimal activity regarding Taspase1 inhibition. rTaspase1 was incubated with the indicated concentrations of either Ac-KISQLD-aldehyde (A) or Ac-ISQLD-cmk (B) for 30 minutes at room temperature. The IVTT, $^{35}$S methionine labeled p75MLL cleavage reporter was then added to 5 ng of pretreated rTaspase1 for 30 minutes at 30° C. The resulting cleavage of p75MLL was resolved by SDS-PAGE and monitored by autoradiography. (C) The structure of an active ISQLD-derived Taspase1 inhibitor Ac-ISQLD-vinyl sulfone is illustrated. (D) Bortezomib has no activity against Taspase1. rTaspase1 was incubated with the indicated concentrations of Bortezomib for 30 minutes at room temperature. The IVTT, $^{35}$S methionine labeled p75MLL cleavage reporter was then added to 5 ng of pretreated rTaspase1 for 30 minutes at 30° C. The resulting cleavage of p75MLL was resolved by SDS-PAGE and monitored by autoradiography.
Figure 2:
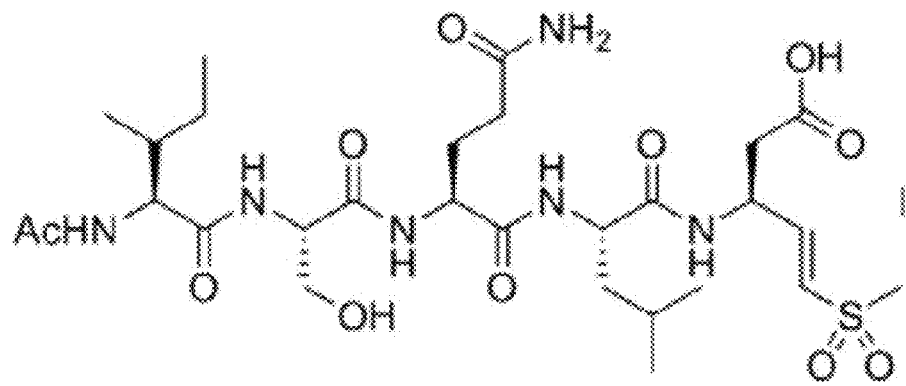
Figure 2:
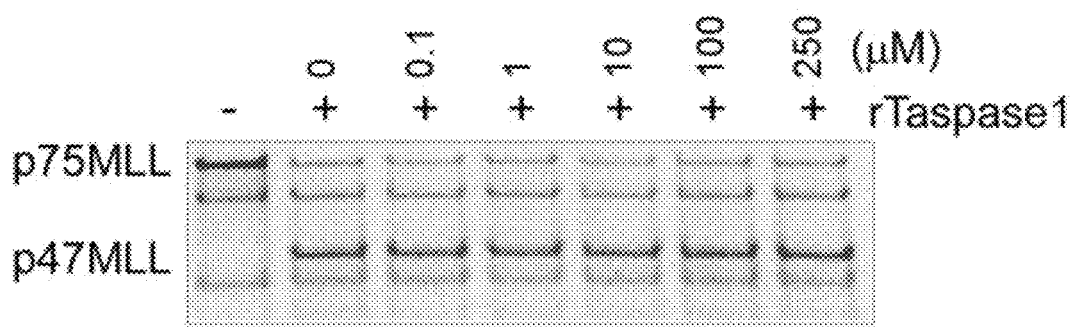

Based on the characterization of Taspase1 cleavage motif, peptide derivatives of ISQLD carrying various protease-specific functional groups (war heads), including aldehyde, chloromethylketone (cmk), vinyl sulfone, vinyl ketone, epoxyketone, and boronate, were synthesized and tested for their ability to inhibit Taspase1 in vitro. The IVTT, $^{35}$S methionine labeled aa 2,400-2,900 of human MLL1 was employed as the cleavage reporter (p75MLL) [4]. Although aldehyde and cmk are effective war heads against general classes of proteases, ISQLD-aldehyde and -cmk were minimally active in inhibiting Taspase1 ($IC_{50}$>100 µM) (FIG. 2A, 2B). Among tested peptidomimetics, ISQLD-vinyl sulfone is most active ($IC_{50}$=29.4 µM) (FIG. 2C) [5]. Consistent with the lack of activity of ISQLD-boronate [5], bortezomib—a boronic acid containing chemotherapeutic drug that targets active site threonine of proteasome—has no activity against Taspase1 (FIG. 2D). Although the in vivo application of ISQLD-vinyl sulfone was limited by its relatively low potency and cell permeability, such proof of principal approach offers invaluable insight into the mechanism by which Taspase1 recognizes its substrates and the future development of Taspase1 inhibitors.

Example 3

Development of a Cell-Based Proteolytic Screen for Taspase1 Inhibitors

Figure 3:
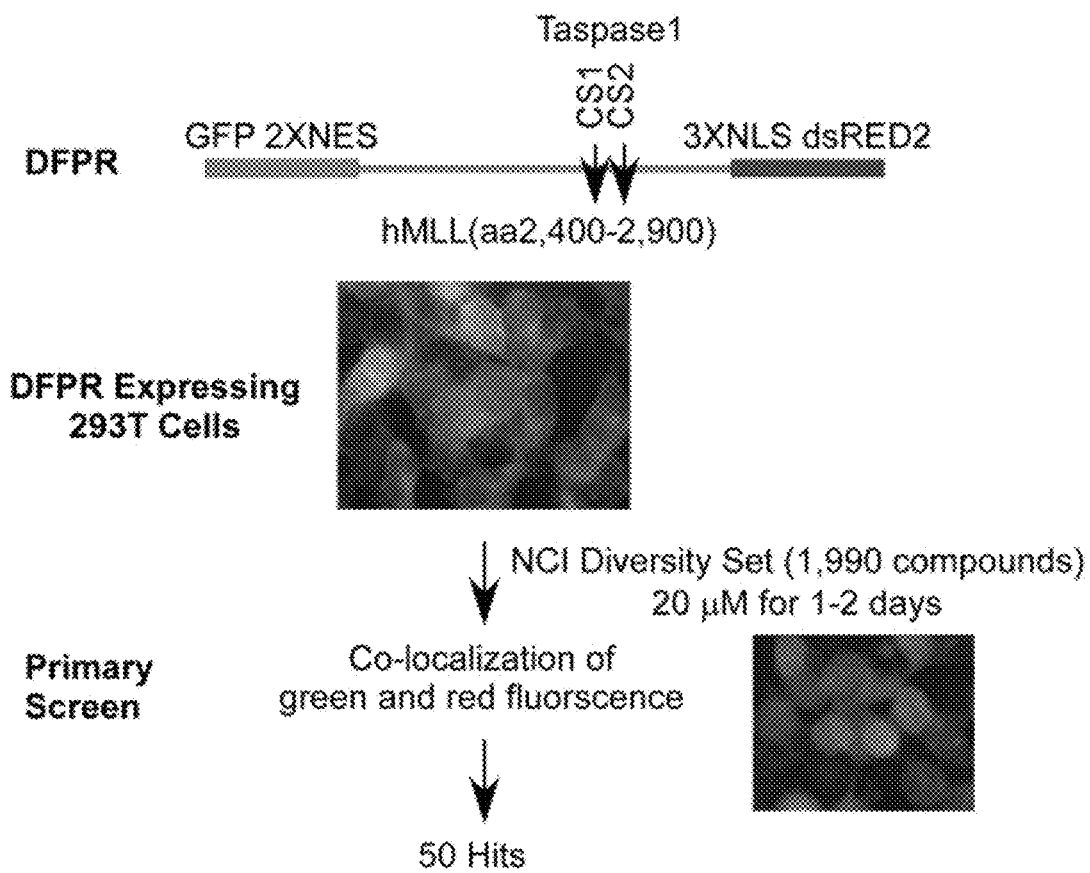
FIG. 3 depicts the design of a dual fluorescent Taspase1 proteolytic reporter (DFPR) assay. Schematics depict the DFPR screen utilized in the identification of small molecule inhibitors of Taspase1. Primary screen, DFPR expressing 293T HEK cells were plated in 96 wells, treated with 20 μM of the NCI DTP Diversity Set 1,990 compounds for 2 days, and the fluorescence was detected by an IX51 fluorescence microscope at day 1 and 2. Pictures of DFPR expressing 293T HEK cells that were either mock treated (DMSO) (top picture) or treated with NSC48300 (bottom picture) are presented.

To identify bioactive, small molecule inhibitors of Taspase1, an in vivo screen was developed in which 293T HEK (human embryonic kidney) cells were engineered to stably express a dual fluorescent Taspase1 proteolytic reporter (DFPR) (FIG. 3). The DFPR (eGFP/NES-p75MLL-NLS/dsRED2) consists of the CS1 & CS2 containing human MLL polypeptide (aa 2,400-2,900, p75MLL) that is flanked by an N-terminal eGFP/NES (nuclear export signal) and a C-terminal NLS (nuclear localization signal)/dsRED2. Upon Taspase1-mediated cleavage, DFPR displays cytosolic green (eGFP/NES-p47) and nuclear red fluorescence (p28-NLS/dsRED2) that can be detected under fluorescence microscopy, whereas upon the inhibition of Taspase1 newly synthesized DFPR could not be cleaved and thus result in increased yellow Example 4

Figure 4:
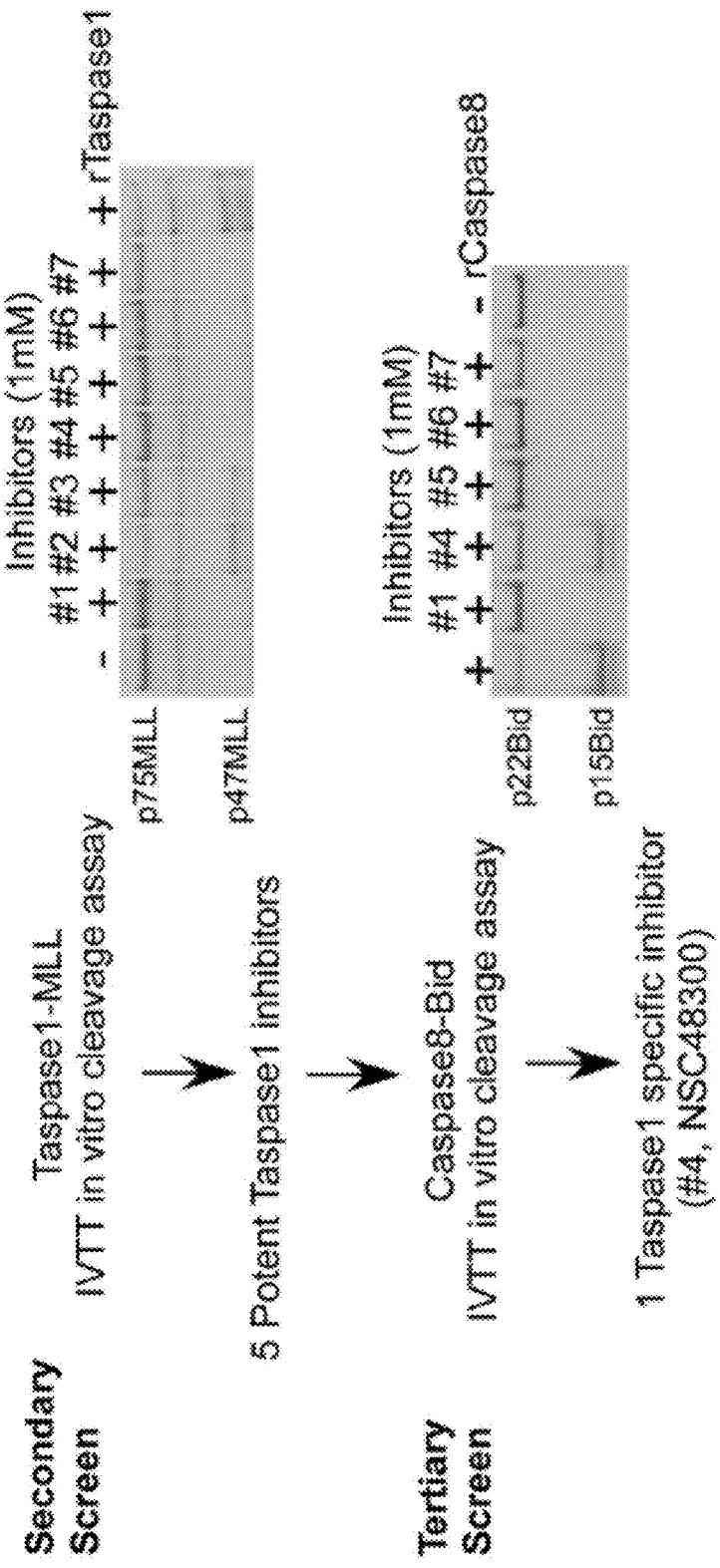
FIG. 4 shows secondary and tertiary screens that were utilized to evaluate the specificity of identified candidate small molecular inhibitors of Taspase1. In the secondary screen, the 50 candidate compounds obtained from the primary screen were tested for their ability to inhibit Taspase1 in vitro. Recombinant Taspase1 (rTaspase1) was incubated with 1 mM of the indicated compounds for 30 minutes at room temperature. The IVTT, $^{35}$S methionine labeled p75MLL cleavage reporter was then added to 15 ng of pretreated rTaspase1 for 30 minutes at 30° C. The resulting cleavage was resolved by SDS-PAGE and monitored by autoradiography. In the tertiary screen, the top 5 chemicals which completely inhibited Taspase1 at 1 mM were tested for their activity against Caspase8. Recombinant Caspase8 (rCaspase8) was incubated with 1 mM of the indicated compounds for 30 minutes at room temperature. The IVTT, $^{35}$S methionine labeled p22Bid cleavage reporter was then added to 250 ng of pretreated rCaspase8 for 2 hours at 30° C. The resulting cleavage was resolved by SDS-PAGE and monitored by autoradiography. Compound #4 (NSC48300) which inhibited Taspase1 but not Caspase8 was designated as TASPIN-NSC48300.

Screen, Identification, and Confirmation of Small Molecule Taspase1 Inhibitors from the NCI Diversity Set Established dual fluorescent Taspase1 proteolytic reporter (DFPR) cells were screened against the NCI Diversity Set 1,990 compounds, which identified 50 candidate inhibitors that induced varying degrees of co-localization of the green and red fluorescence (FIG. 3). To confirm the specific inhibition of Taspase1 by these candidate compounds, a secondary screen was performed using the established Taspase1-MLL in vitro cleavage assay, in which the IVTT, $^{35}$S methionine labeled p75MLL was utilized as the cleavage reporter [4]. Among these candidate inhibitors, five compounds actively inhibited the protease activity of Taspase1 in vitro (FIG. 4). To further characterize these small molecule Taspase1 inhibitors, a tertiary screen was performed, in which the known Caspase-8-mediated cleavage of p22 BID was employed [6]. The IVTT-based Caspase8-BID in vitro cleavage assay was first optimized. Caspase8 was incorporated into the screen based on the fact that Caspases, like Taspase1, also cleave polypeptide after P1 aspartate [7]. Interestingly, four of the five top chemicals are shared Taspase1, Caspase8 inhibitors, whereas compound #4 (NSC48300) only targets Taspase1 (FIG. 4). Taken together, this cell-based in vivo screen followed by two in vitro confirmatory assays identified NSC48300, [4-[(4-arsonophenyl)methyl]phenyl]arsonic acid, as a highly specific small molecule Taspase1 inhibitor which was thus designated as TASPIN-NSC48300.

Example 5

The Structure-Activity Relationship of TASPIN-NSC48300

Figure 5A:
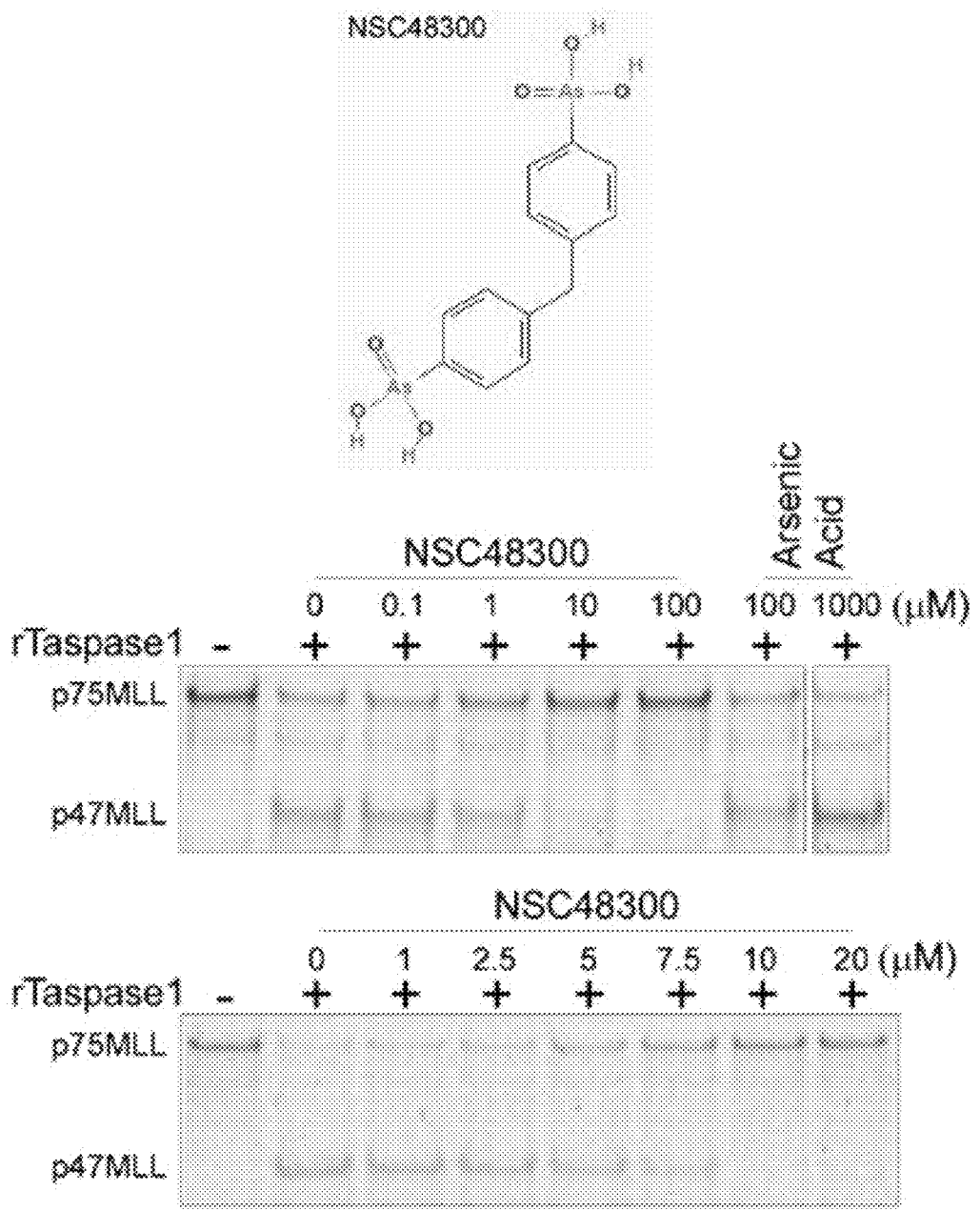
FIG. 5 presents the characterization and the structure-activity relationship of TASPIN-NSC48300. (A) Chemical structure of TASPIN-NSC48300 is shown. 10 μM of NSC48300 completely inhibited Taspase1-mediated p75MLL cleavage in vitro and no inhibition of Taspase1 was observed upon the treatment with 1 mM of arsenic acid. rTaspase1 was incubated with the indicated concentrations of either NSC48300 or arsenic acid for 30 minutes at room temperature. The IVTT, $^{35}$S methionine labeled p75MLL cleavage reporter was then added to 5 ng of pretreated rTaspase1 for 30 minutes at 30° C. The resulting cleavage was resolved by SDS-PAGE and monitored by autoradiography. (B) TASPIN-NSC48300 did not exhibit enhanced inhibition against Taspase1 with increasing pretreatment time. rTaspase1 was incubated with 5 μM of NSC48300 for the indicated times at room temperature. The IVTT, $^{35}$S methionine labeled p75MLL cleavage reporter was then added to 5 ng of pretreated rTaspase1 for 30 minutes at 30° C. The resulting cleavage of p75MLL was resolved by SDS-PAGE and monitored by autoradiography. (C) rTaspase1 was incubated with the indicated concentrations of individual TASPIN-NSC48300 analogues for 30 minutes at room temperature. The IVTT, $^{35}$S methionine labeled p75MLL cleavage reporter was then added to 5 ng of pretreated rTaspase1 for 30 minutes at 30° C. The resulting cleavage of p75MLL was resolved by SDS-PAGE and monitored by autoradiography.
Figure 5B:
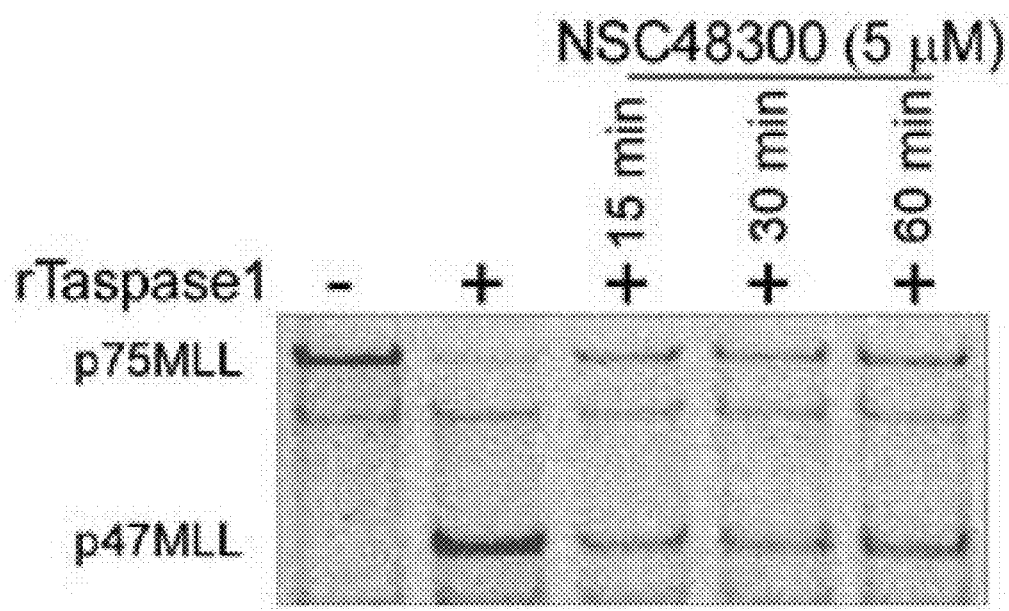
Figure 5C:
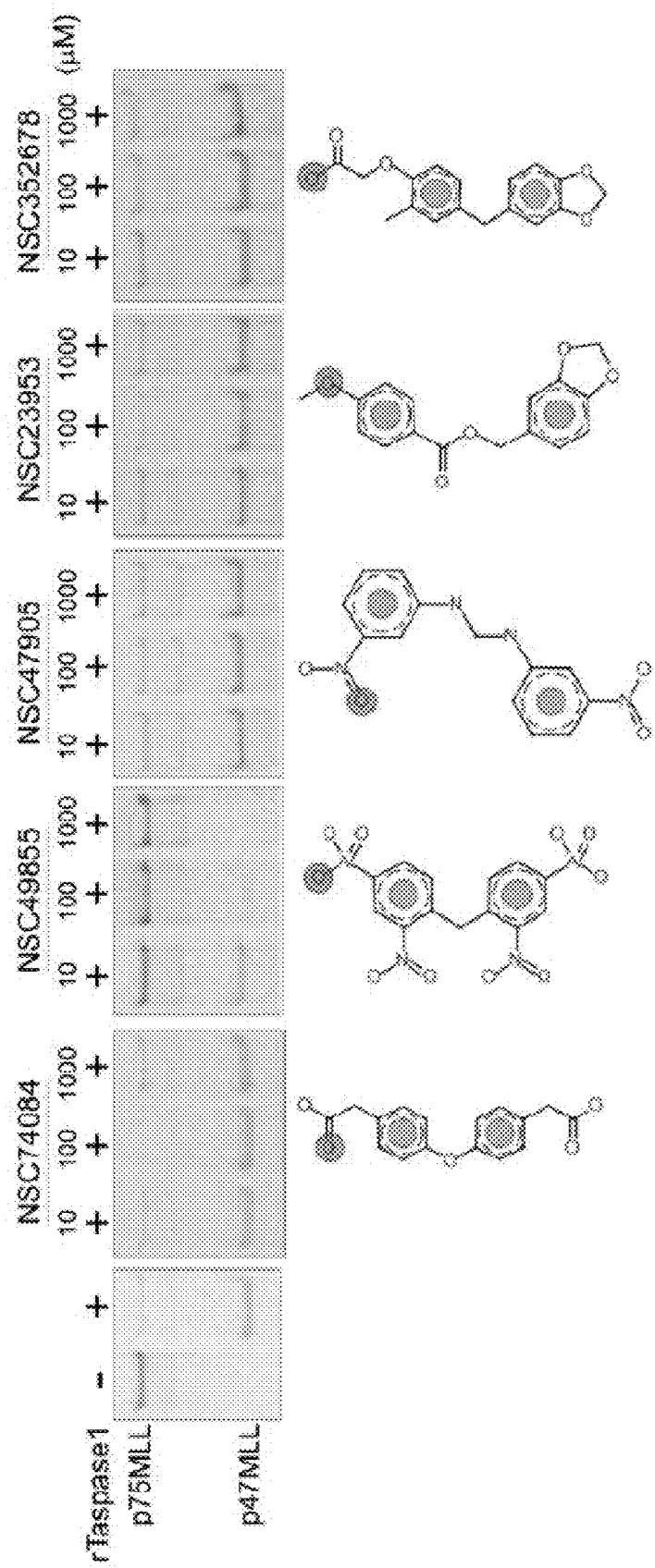

The combined in vivo and in vitro screen identified a specific Taspase1 inhibitor TASPIN-NSC48300. The activity of NSC48300 was further evaluated using the IVTT, $^{35}$S methionine labeled p75MLL reporter. TASPIN-NSC48300 ($IC_{50}$=~7.5 µM) is more potent than ISQLD-vinyl sulfone (1050=29.4 µM) in Taspase1 inhibition (FIG. 5A). Pre-incubation of Taspase1 with NSC48300 for increasing periods of time did not enhance the inhibition, indicating that NSC48300 is unlikely to act as a covalent irreversible inhibitor (FIG. 5B). As TASPIN-NSC48300 is an arsonic acid containing compound, we assessed whether free arsenic acid can inactivate Taspase1. Up to 1 mM of arsenic acid was utilized and no inhibition of Taspase1 was observed (FIG. 5A). Nevertheless, the arsonic acid moiety of TASPIN-NSC48300 is essential as NSC48300 analogue NSC74084 had no demonstrable activity (FIG. 5C). Furthermore, modifications of the benzene ring of arylarsonic acid (NSC49855) compromised the inhibitory activity (FIG. 5C). In summary, this structure-activity relationship study indicated that arsonic acid may serve as an active functional group against threonine proteases when conjugated with appropriate chemical backbones such as a benzene ring.

Example 6

Figure 6:
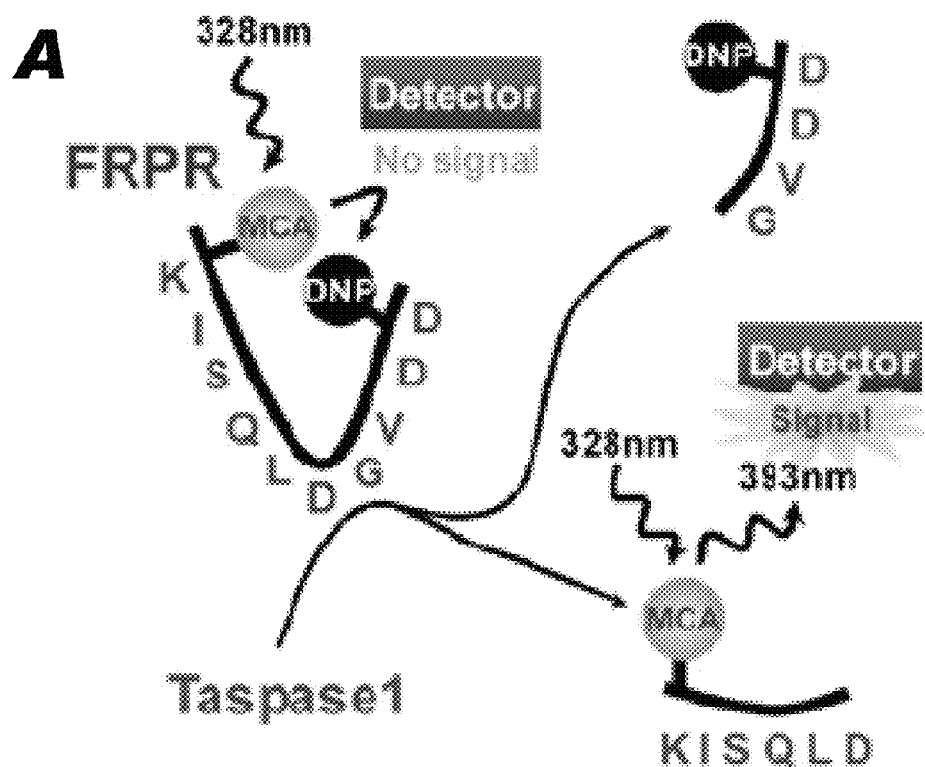
FIG. 6 illustrates the enzyme kinetics analysis of TASPIN-NSC48300 by a FRET-based Taspase1 proteolytic reporter assay (FRPR). (A) Diagram depicts the FRET-based Taspase1 proteolytic reporter (FRPR). (B) Taspase1-mediated cleavage of FRPR results in increasing fluorescence over time. 15 μM of FRPR was incubated with 100 nM of rTaspase1 at room temperature and the resulting steady state fluorescence was monitored by a Perkin Elmer LS55 fluorescence spectrometer. (C) The inhibition of Taspase1 by TASPIN-NSC48300. Increasing amounts of FRPR were incubated with 100 nM of rTaspase1 that was pretreated with the indicated amounts of NSC48300. The enzymatic activity was monitored by a Perkin Elmer LS55 fluorescence spectrometer. The $K_M$ and $K_I$ were calculated using GraphPad Prism software. AU denotes absolute fluorescence unit. Data presented in (C) were mean±s.d. of three independent experiments.
Figure 6:
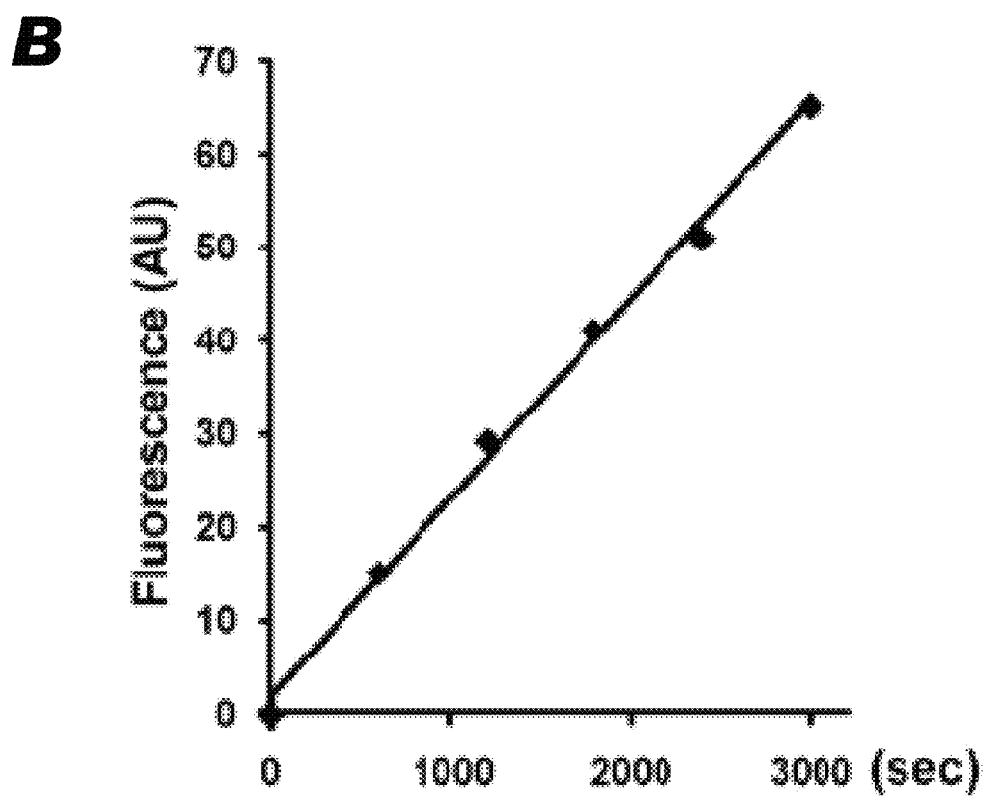
Figure 6C:
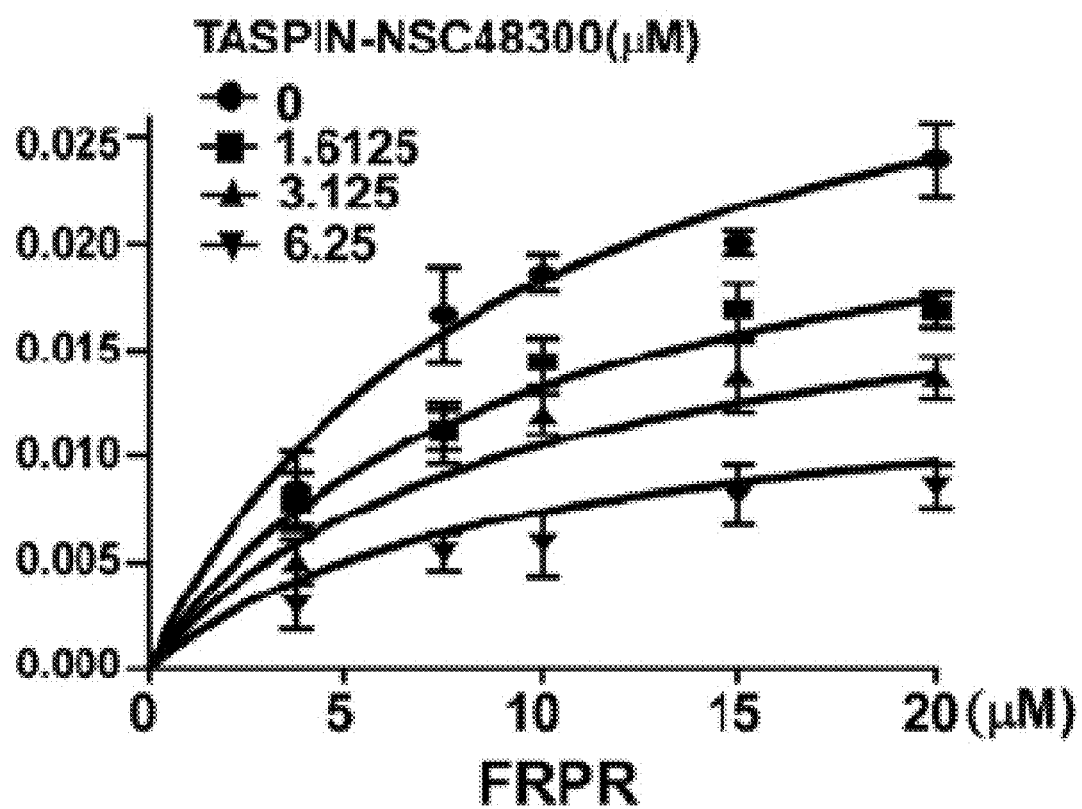

Enzyme Kinetics Analysis of TASPIN-NSC48300 Using a FRET-Based Taspase1 Cleavage Reporter To probe into the mechanisms by which TASPIN-NSC48300 inhibits Taspase1 and to enable detailed kinetics analysis, a FRET (Fluorescence Resonance Energy Transfer)-based in vitro Taspase1 cleavage assay was modified [8]. This FRET-based Taspase1 proteolytic reporter (FRPR, MCA-KISQLDGVDD-DNP) consists of a 10 aa CS2 consensus sequence conjugated with a fluorogenic coumarin (MCA) group and a 2,4-dinitrophenyl (DNP) quenching group at its N- and C-terminus, respectively (FIG. 6A). Upon Taspase1-mediated cleavage, MCA is no longer quenched by DNP, resulting in fluorescence that can be excited at 328 nm and detected at 393 nm wavelengths. The apparent $K_M$ of the FRPR is 9.06±2.80 μM (FIG. 6B). By incubating varying concentrations of FRPR and TASPIN-NSC48300, a non-competitive inhibition of Taspase1 by NSC48300 with a $K_I$ at 4.22±0.46 μM was demonstrated (FIG. 6C). The discovery of TASPIN-NSC48300 as a non-competitive inhibitor indicates the existence of yet characterized allosteric sites of Taspase1.

Example 7

Figure 7:
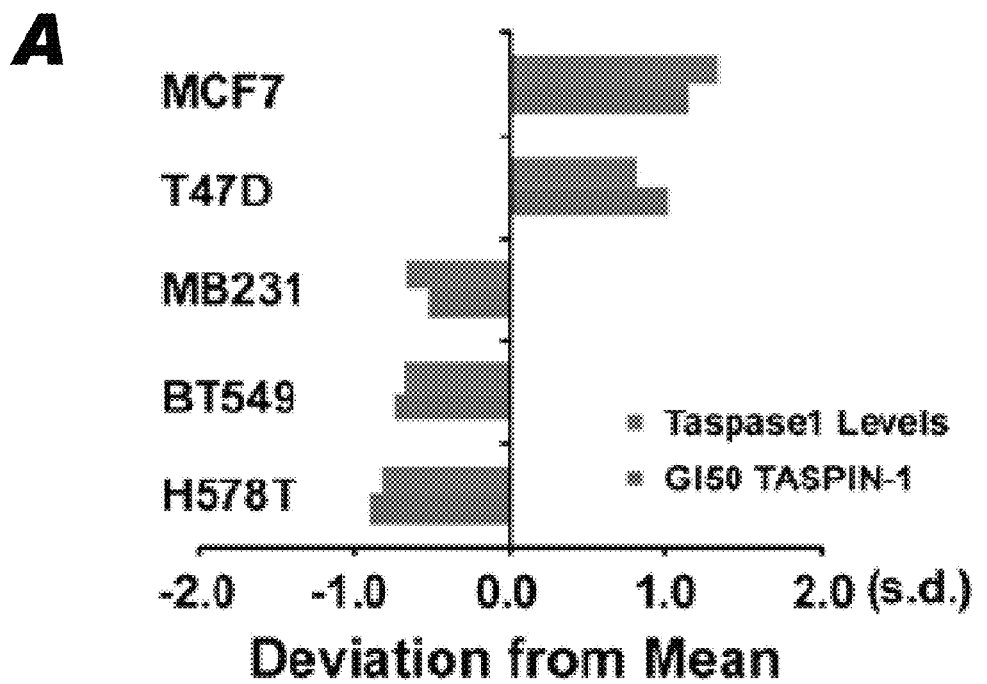
FIG. 7 shows the positive correlation between NSC-48300 induced growth inhibition and the protein level of Taspase1. (A, B) Comparison of normalized Taspase1 protein expression with the GI50 concentration of NSC48300 demonstrated that the sensitivity of growth inhibition to NSC48300 correlates well with the protein expression of Taspase1 in breast (A) and brain (B) cancer cell lines. Protein expression data of Taspase1 in NCI60 cell lines has been described by Saklatvala et al., 2002, Biochem, Soc. Symposium, 70, while GI50 data are obtained from the NCI DTP website (dtp.nci.nih.gov). The protein expression and the GI50 of individual breast and brain cancer cell line are compared to the mean of all five breast cancer cell lines and all five brain cancer cell lines, respectively. Protein expression: individual expression-mean expression. GI50: mean (GI50)log 10-individual (GI50)log 10). Data are presented as a fraction of the standard deviation. GI50 denotes growth inhibition 50%. (C) SV-40 Transformed MEFs of the indicated genotypes were treated with the indicated concentrations of TASPIN-NSC48300 for 2 days and the relative cell number was measured using MTT assays. The cell number of mock-treated wells was assigned as 1. * denotes p value <0.05. Data presented in were mean±s.d. of three independent experiments.
Figure 7:
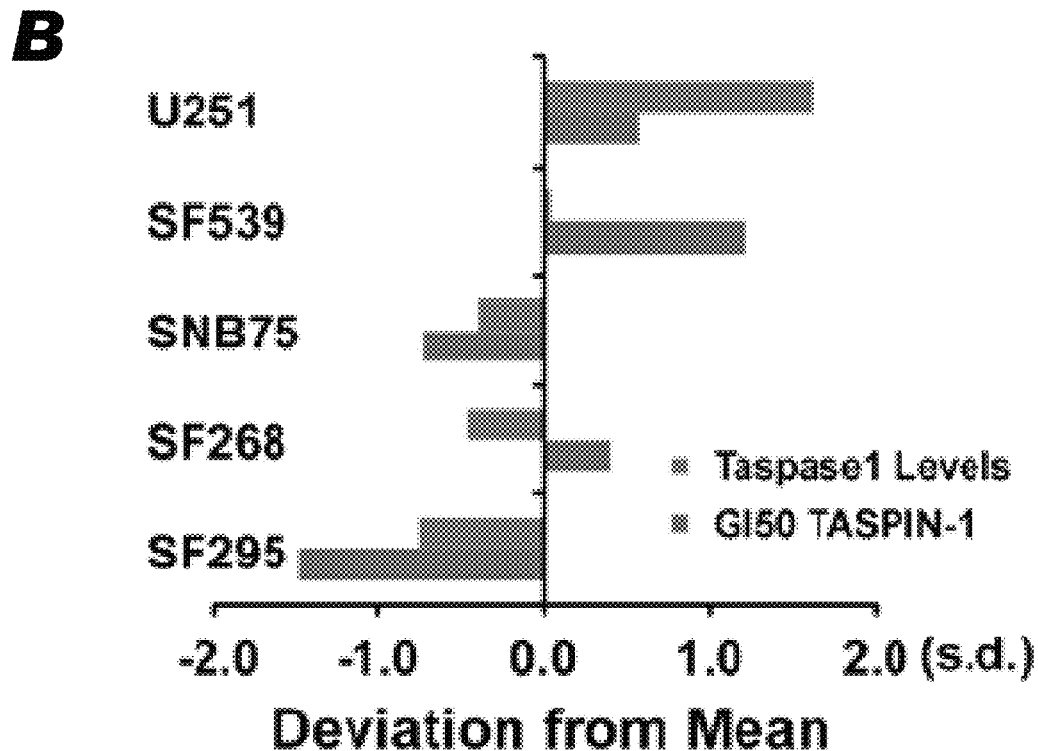
Figure 7C:
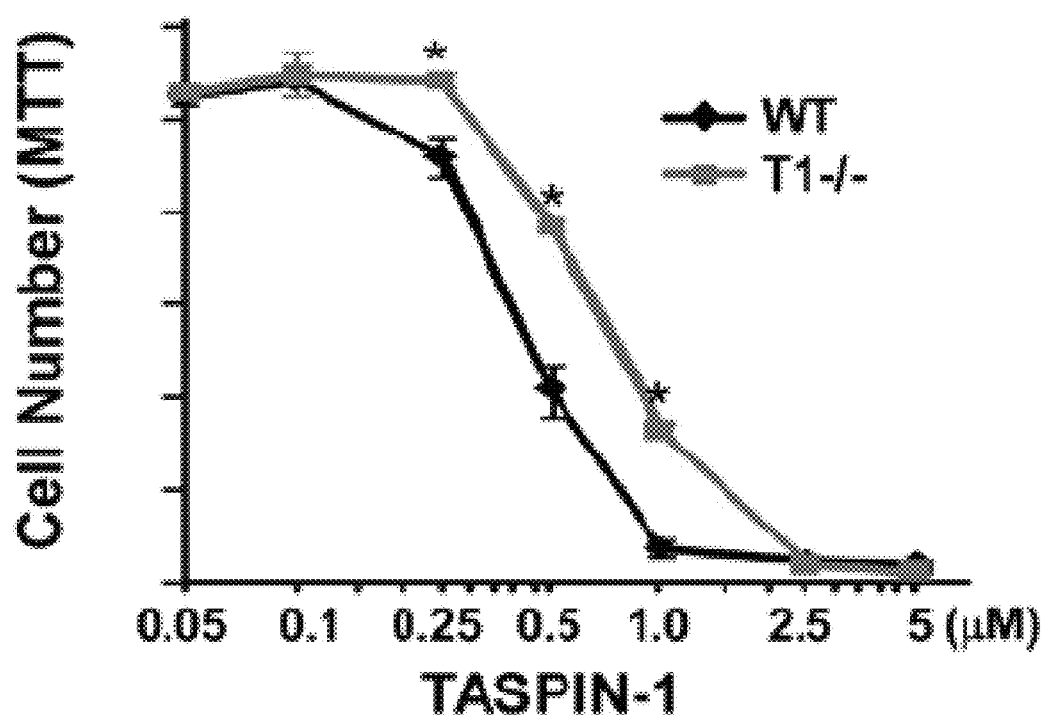

The Ability of TASPIN-NSC48300 to Inhibit Cellular Proliferation Correlates with the Expression of Taspase1 in Breast and Brain Cancer Cell Lines According to the database published by the NCI Developmental Therapeutic Program (DTP) (dtp.nci.nih.gov), TASPIN-NSC48300 produced a distinct pattern of growth inhibition in the NCI60 in vitro anticancer drug screen operated by the NCI Developmental Therapeutic Program [9]. Remarkably, the sensitivity to TASPIN-NSC48300-mediated growth inhibition correlates closely with the protein level of Taspase1 in human breast and brain cancer cell lines (FIG. 7A, 7B) [1]. In agreement with the notion that Taspase1 is the major target of TASPIN-NSC48300 in blocking cancer cell proliferation, SV40-transformed wild-type mouse embryonic fibroblasts (MEFs) are more susceptible to NSC48300 than SV40-transformed Taspase1$^{-/-}$ MEFs (FIG. 7C). Due to the nature of its relatively simple chemical composition, TASPIN-NSC48300 likely targets more than one cellular proteins or pathways. In fact, NSC48300 was recently shown to inhibit autotoxin, an extracellular protein, involved in cellular migration but not proliferation [10]. Altogether, the known generalized anti-tumor effect of NSC48300 is likely contributed by the inactivation of Taspase1.

Example 8

Screen, Identification, and Confirmation of Small Molecule Taspase1 Inhibitors from a Maybridge 17K Sample Library Approximately 17,000 compounds from a Maybridge 17K library were screened using the FRET-based high throughput screen described in Example 6. The compounds were tested at concentration of 100, 10, 1, and 0.1 μM. Compounds with $EC_{50}<10$ μM were selected for confirmation in detailed dose-response assays and counter screen. This analysis identified 31 compounds as effective Taspase1 inhibitors. TABLE 1 presents the structures and $EC_{50}$ values for the most effective inhibitors.

TABLE 1

Maybridge Library Screen Results.

| Name | Structure | $EC_{50}$ (μM) |
|---|---|---|
| BTB 00807 | 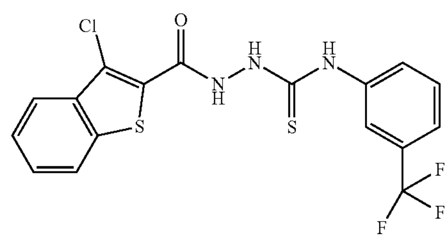 [SMILES: O=C(NNC(=S)Nc1cccc(C(F)(F)F)c1)c1sc2ccccc2c1Cl] | 9.9 |
| SPB 08132 | 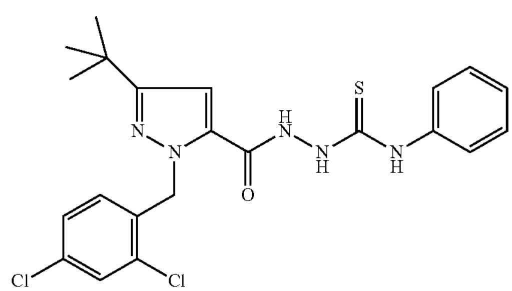 [SMILES: CC(C)(C)c1cc(C(=O)NNC(=S)Nc2ccccc2)n(Cc2ccc(Cl)cc2Cl)n1] | 5.9 |
| RJF 02020 | 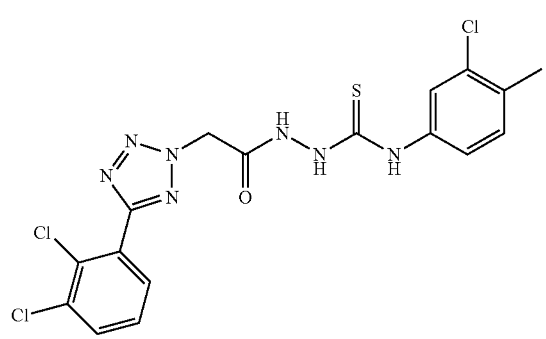 [SMILES: Cc1ccc(NC(=S)NNC(=O)Cn2nnc(-c3cccc(Cl)c3Cl)n2)cc1Cl] | 3.9 |

TABLE 1-continued

Maybridge Library Screen Results.

| Name | Structure | EC$_{50}$ (µM) |
|---|---|---|
| CD 06082 | 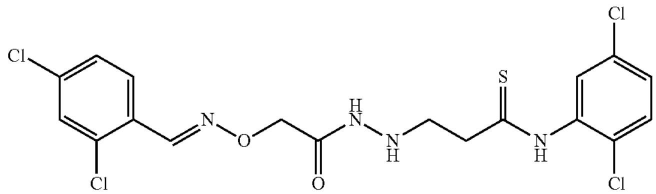 [SMILES: O=C(CO/N=C/c1ccc(Cl)cc1Cl)NNCCC(=S)Nc1cc(Cl)ccc1Cl] | 3.3 |
| CD 02506 | 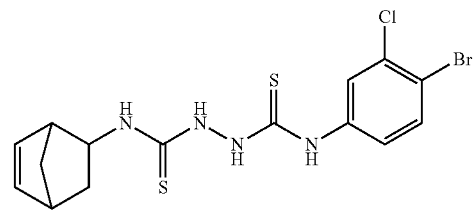 [SMILES: S=C(NNC(=S)NC1CC2C=CC1C2)Nc1ccc(Br)c(Cl)c1] | 1.5 |
| HTS 06900 | 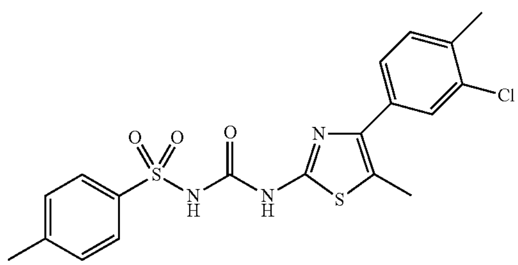 [SMILES: Cc1ccc(S(=O)(=O)NC(=O)Nc2nc(-c3ccc(C)c(Cl)c3)c(C)s2)cc1] | 4.0 |
| HTS 01888 | 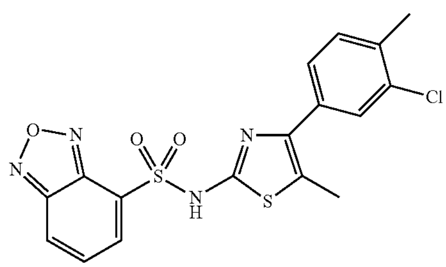 [SMILES: Cc1ccc(-c2nc(NS(=O)(=O)c3cccc4nonc34)sc2C)cc1Cl] | 2.2 |

REFERENCES

1. Takeda S, Chen D Y, Westergard T D, Fisher J K, Rubens J A, et al. (2006) Proteolysis of MLL family proteins is essential for taspase1-orchestrated cell cycle progression. Genes Dev 20: 2397-2409.
2. Niehof M, Borlak J (2008) EPS15R, TASP1, and PRPF3 are novel disease candidate genes targeted by HNF4alpha splice variants in hepatocellular carcinomas. Gastroenterology 134: 1191-1202.
3. Scrideli C A, Carlotti C G, Jr., Okamoto O K, Andrade V S, Cortez M A, et al. (2008) Gene expression profile analysis of primary glioblastomas and non-neoplastic brain tissue: identification of potential target genes by oligonucleotide microarray and real-time quantitative PCR. J Neurooncol 88: 281-291.
4. Hsieh J J, Cheng E H, Korsmeyer S J (2003) Taspase1: a threonine aspartase required for cleavage of MLL and proper HOX gene expression. Cell 115: 293-303.
5. Lee J T, Chen D Y, Yang Z, Ramos A D, Hsieh J J, et al. (2009) Design, syntheses, and evaluation of Taspase1 inhibitors. Bioorg Med Chem Lett 19: 5086-5090.
6. Zha J, Weiler S, Oh K J, Wei M C, Korsmeyer S J (2000) Posttranslational N-myristoylation of BID as a molecular switch for targeting mitochondria and apoptosis. Science 290: 1761-1765.
7. Thornberry N A, Rano T A, Peterson E P, Rasper D M, Timkey T, et al. (1997) A combinatorial approach defines specificities of members of the caspase family and granzyme B. Functional relationships established for key mediators of apoptosis. J Biol Chem 272: 17907-17911.
8. Khan J A, Dunn B M, Tong L (2005) Crystal structure of human Taspase1, a crucial protease regulating the function of MLL. Structure 13: 1443-1452.
9. Shoemaker R H (2006) The NCI60 human tumour cell line anticancer drug screen. Nat Rev Cancer 6: 813-823.
10. Saunders L P, Ouellette A, Bandle R, Chang W C, Zhou H, et al. (2008) Identification of small-molecule inhibitors of autotaxin that inhibit melanoma cell migration and invasion. Mol Cancer Ther 7: 3352-3362.

What is claimed is:

1. A method for reducing the growth rate of a neoplasm expressing taspase 1, the method comprising contacting the neoplasm with a therapeutic amount of a compound selected from the group consisting of:

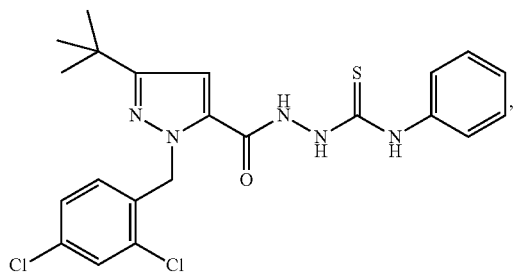

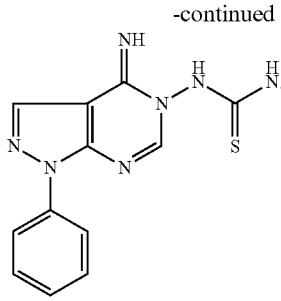

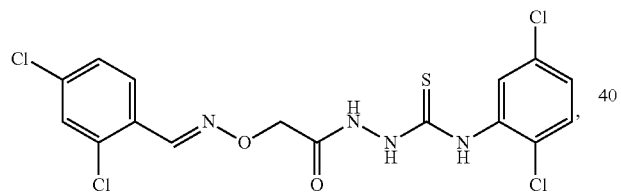

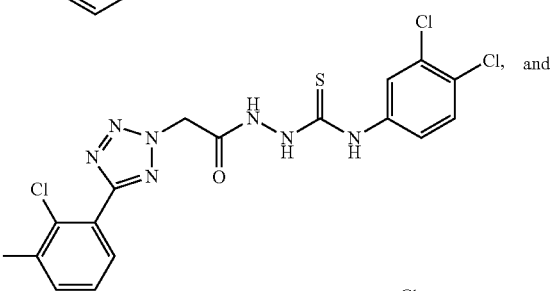

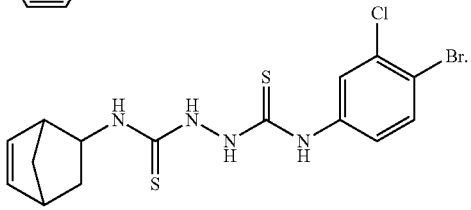

* * * * *